(12) United States Patent
Hoarau (10) Patent No.: US 8,260,391 B2
(45) Date of Patent: Sep. 4, 2012

(54) MEDICAL SENSOR FOR REDUCING MOTION ARTIFACTS AND TECHNIQUE FOR USING THE SAME

(75) Inventor: Carine Hoarau, Lafayette, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 107 days.

(21) Appl. No.: 12/836,306

(22) Filed: Jul. 14, 2010

(65) Prior Publication Data

US 2010/0280344 A1 Nov. 4, 2010

Related U.S. Application Data

(63) Continuation of application No. 11/225,295, filed on Sep. 12, 2005, now abandoned.

(51) Int. Cl.
*A61B 5/1455* (2006.01)
(52) U.S. Cl. .................................. 600/344; 600/323
(58) Field of Classification Search .............. 600/310, 600/322, 323, 344
See application file for complete search history.

(56) References Cited

U.S. PATENT DOCUMENTS

| | | | |
|---|---|---|---|
| D222,454 S | 10/1971 | Beeber | |
| D250,275 S | 11/1978 | Bond | |
| D251,387 S | 3/1979 | Ramsey et al. | |
| 4,289,141 A | 9/1981 | Cormier | |
| D262,488 S | 12/1981 | Rossman et al. | |
| 4,471,538 A * | 9/1984 | Pomeranz et al. | 2/159 |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,677,528 A | 6/1987 | Miniet | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,722,120 A | 2/1988 | Lu | |
| 4,726,382 A | 2/1988 | Boehmer et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,783,815 A | 11/1988 | Buttner | |

(Continued)

FOREIGN PATENT DOCUMENTS

DE 3405444 8/1985

(Continued)

OTHER PUBLICATIONS

International Search Report mailed Jun. 8, 2002 for PCT/US02/07759.

(Continued)

*Primary Examiner* — Eric Winakur
(74) *Attorney, Agent, or Firm* — Fletcher Yoder (57) ABSTRACT

A sensor may be adapted to reduce motion artifacts by damping the effects of outside forces and sensor motion. A sensor is provided with a motion damping structure adapted to reduce the effect of motion of a sensor emitter and/or detector. Further, a method of damping outside forces and sensor motion is also provided.

17 Claims, 4 Drawing Sheets

U.S. PATENT DOCUMENTS

| | | |
|---|---|---|
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynki |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |

| Patent No. | Date | Inventor(s) |
|---|---|---|
| 5,413,100 A | 5/1995 | Barthelemy et al. |
| 5,413,101 A | 5/1995 | Sugiura |
| 5,413,102 A | 5/1995 | Schmidt et al. |
| 5,416,582 A | 5/1995 | Knutson et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,788,634 A | 8/1998 | Suda et al. |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,179 A | 10/1998 | Lichter et al. |
| 5,827,182 A | 10/1998 | Raley et al. |
| 5,829,439 A | 11/1998 | Yokosawa et al. |
| 5,830,135 A | 11/1998 | Bosque et al. |
| 5,830,136 A | 11/1998 | Delonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |

| Patent | Date | Inventor |
|---|---|---|
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Well |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,075,610 A | 6/2000 | Ueda et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllermann et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grinblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |

| | | |
|---|---|---|
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 * | 10/2002 | Schnall .......... 600/342 |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |

| | | | | | | |
|---|---|---|---|---|---|---|
| 6,735,459 B2 | 5/2004 | Parker | | 7,027,850 B2 | 4/2006 | Wasserman |
| 6,745,060 B2 | 6/2004 | Diab et al. | | 7,039,449 B2 | 5/2006 | Al-Ali |
| 6,745,061 B1 | 6/2004 | Hicks et al. | | 7,043,289 B2 | 5/2006 | Fine et al. |
| 6,748,253 B2 | 6/2004 | Norris et al. | | 7,047,055 B2 | 5/2006 | Boas et al. |
| 6,748,254 B2 | 6/2004 | O'Neill et al. | | 7,060,035 B2 | 6/2006 | Wasserman |
| 6,754,515 B1 | 6/2004 | Pologe | | 7,062,307 B2 | 6/2006 | Norris et al. |
| 6,754,516 B2 | 6/2004 | Mannheimer | | 7,067,893 B2 | 6/2006 | Mills et al. |
| 6,760,607 B2 | 7/2004 | Al-Ali | | 7,072,701 B2 | 7/2006 | Chen et al. |
| 6,760,609 B2 | 7/2004 | Jacques | | 7,072,702 B2 | 7/2006 | Edgar, Jr. et al. |
| 6,760,610 B2 | 7/2004 | Tscupp et al. | | 7,072,705 B2 | 7/2006 | Miga et al. |
| 6,763,255 B2 | 7/2004 | DeLonzor et al. | | 7,079,880 B2 | 7/2006 | Stetson |
| 6,763,256 B2 | 7/2004 | Kimball et al. | | 7,085,597 B2 | 8/2006 | Fein et al. |
| 6,770,028 B1 | 8/2004 | Ali et al. | | 7,096,052 B2 | 8/2006 | Mason et al. |
| 6,771,994 B2 | 8/2004 | Kiani et al. | | 7,096,054 B2 | 8/2006 | Abdul-Hafiz et al. |
| 6,773,397 B2 | 8/2004 | Kelly | | 7,107,088 B2 | 9/2006 | Aceti |
| 6,778,923 B2 | 8/2004 | Norris et al. | | 7,113,815 B2 | 9/2006 | O'Neil et al. |
| 6,780,158 B2 | 8/2004 | Yarita | | 7,123,950 B2 | 10/2006 | Mannheimer |
| 6,791,689 B1 | 9/2004 | Weckstrom | | 7,127,278 B2 | 10/2006 | Melker et al. |
| 6,792,300 B1 | 9/2004 | Diab et al. | | 7,130,671 B2 | 10/2006 | Baker, Jr. et al. |
| 6,801,797 B2 | 10/2004 | Mannheimer et al. | | 7,132,641 B2 | 11/2006 | Schulz et al. |
| 6,801,798 B2 | 10/2004 | Geddes et al. | | 7,133,711 B2 | 11/2006 | Chernoguz et al. |
| 6,801,799 B2 | 10/2004 | Mendelson | | 7,139,559 B2 | 11/2006 | Kenagy et al. |
| 6,801,802 B2 | 10/2004 | Sitzman et al. | | 7,142,901 B2 | 11/2006 | Kiani et al. |
| 6,802,812 B1 | 10/2004 | Walker et al. | | 7,162,288 B2 | 1/2007 | Nordstrom et al. |
| 6,805,673 B2 | 10/2004 | Dekker | | 7,190,987 B2 | 3/2007 | Kindekugel et al. |
| 6,810,277 B2 | 10/2004 | Edgar, Jr. et al. | | 7,198,778 B2 | 4/2007 | Achilefu et al. |
| 6,813,511 B2 | 11/2004 | Diab et al. | | 7,215,984 B2 | 5/2007 | Diab et al. |
| 6,816,741 B2 | 11/2004 | Diab | | 7,225,006 B2 | 5/2007 | Al-Ali et al. |
| 6,819,950 B2 | 11/2004 | Mills | | 7,228,161 B2 | 6/2007 | Chin |
| 6,822,564 B2 | 11/2004 | Al-Ali | | 7,236,811 B2 | 6/2007 | Schmitt et al. |
| 6,825,619 B2 | 11/2004 | Norris | | 7,238,159 B2 * | 7/2007 | Banet et al. ............... 600/324 |
| 6,826,419 B2 | 11/2004 | Diab et al. | | 7,248,910 B2 | 7/2007 | Li et al. |
| 6,829,496 B2 | 12/2004 | Nagai et al. | | 7,254,433 B2 | 8/2007 | Diab et al. |
| 6,830,711 B2 | 12/2004 | Mills et al. | | 7,254,434 B2 | 8/2007 | Schulz et al. |
| 6,836,679 B2 | 12/2004 | Baker, Jr. et al. | | 7,280,858 B2 | 10/2007 | Al-Ali et al. |
| 6,839,579 B1 | 1/2005 | Chin | | 7,295,866 B2 | 11/2007 | Al-Ali |
| 6,839,580 B2 | 1/2005 | Zonios et al. | | 7,305,262 B2 | 12/2007 | Brodnick et al. |
| 6,839,582 B2 | 1/2005 | Heckel | | 7,315,753 B2 | 1/2008 | Baker, Jr. et al. |
| 6,839,659 B2 | 1/2005 | Tarassenko et al. | | 7,412,272 B2 | 8/2008 | Medina |
| 6,842,635 B1 | 1/2005 | Parker | | 2002/0016537 A1 | 2/2002 | Muz et al. |
| 6,845,256 B2 | 1/2005 | Chin et al. | | 2002/0026109 A1 | 2/2002 | Diab et al. |
| 6,850,788 B2 | 2/2005 | Al-Ali | | 2002/0028990 A1 | 3/2002 | Sheperd et al. |
| 6,850,789 B2 | 2/2005 | Schweitzer, Jr. et al. | | 2002/0038078 A1 | 3/2002 | Ito |
| 6,861,639 B2 | 3/2005 | Al-Ali | | 2002/0042558 A1 | 4/2002 | Mendelson |
| 6,863,652 B2 | 3/2005 | Huang et al. | | 2002/0068859 A1 | 6/2002 | Knopp |
| 6,865,407 B2 | 3/2005 | Kimball et al. | | 2002/0072681 A1 | 6/2002 | Schnall |
| 6,879,850 B2 | 4/2005 | Kimball | | 2002/0116797 A1 | 8/2002 | Modgil et al. |
| 6,882,874 B2 | 4/2005 | Huiku | | 2002/0128544 A1 | 9/2002 | Diab et al. |
| 6,898,452 B2 | 5/2005 | Al-Ali et al. | | 2002/0133067 A1 | 9/2002 | Jackson, III |
| 6,909,912 B2 | 6/2005 | Melker et al. | | 2002/0156354 A1 | 10/2002 | Larson |
| 6,912,413 B2 | 6/2005 | Rantala et al. | | 2002/0161287 A1 | 10/2002 | Schmitt |
| 6,920,345 B2 | 7/2005 | Al-Ali et al. | | 2002/0173706 A1 | 11/2002 | Takatani |
| 6,931,269 B2 | 8/2005 | Terry | | 2002/0190863 A1 | 12/2002 | Lynn |
| 6,934,570 B2 | 8/2005 | Kiani et al. | | 2003/0018243 A1 | 1/2003 | Gerhardt et al. |
| 6,939,307 B1 | 9/2005 | Dunlop | | 2003/0036690 A1 | 2/2003 | Geddes et al. |
| 6,941,162 B2 | 9/2005 | Fudge et al. | | 2003/0045785 A1 | 3/2003 | Diab et al. |
| 6,947,781 B2 | 9/2005 | Asada et al. | | 2003/0073889 A1 | 4/2003 | Keilbach et al. |
| 6,950,687 B2 | 9/2005 | Al-Ali | | 2003/0073890 A1 | 4/2003 | Hanna |
| 6,954,664 B2 | 10/2005 | Sweitzer | | 2003/0100840 A1 | 5/2003 | Sugiura et al. |
| 6,968,221 B2 | 11/2005 | Rosenthal | | 2003/0181799 A1 | 9/2003 | Lindekugel et al. |
| 6,979,812 B2 | 12/2005 | Al-Ali | | 2003/0187337 A1 | 10/2003 | Tarassenko et al. |
| 6,983,178 B2 | 1/2006 | Fine et al. | | 2003/0197679 A1 | 10/2003 | Ali et al. |
| 6,985,763 B2 | 1/2006 | Boas et al. | | 2003/0212316 A1 | 11/2003 | Leiden et al. |
| 6,985,764 B2 | 1/2006 | Mason et al. | | 2003/0220548 A1 | 11/2003 | Schmitt et al. |
| 6,990,426 B2 | 1/2006 | Yoon et al. | | 2003/0225323 A1 | 12/2003 | Kiani et al. |
| 6,992,751 B2 | 1/2006 | Okita et al. | | 2004/0006261 A1 | 1/2004 | Swedlow et al. |
| 6,992,772 B2 | 1/2006 | Block | | 2004/0024326 A1 | 2/2004 | Yeo et al. |
| 6,993,371 B2 | 1/2006 | Kiani et al. | | 2004/0039272 A1 | 2/2004 | Abdul-Hafiz et al. |
| 6,993,372 B2 | 1/2006 | Fine et al. | | 2004/0039273 A1 | 2/2004 | Terry |
| 6,996,427 B2 | 2/2006 | Ali et al. | | 2004/0054291 A1 | 3/2004 | Schulz et al. |
| 7,003,338 B2 | 2/2006 | Weber et al. | | 2004/0059209 A1 | 3/2004 | Al-Ali et al. |
| 7,003,339 B2 | 2/2006 | Diab et al. | | 2004/0068164 A1 | 4/2004 | Diab et al. |
| 7,006,855 B1 | 2/2006 | Sarussi | | 2004/0092805 A1 | 5/2004 | Yarita |
| 7,006,856 B2 | 2/2006 | Baker, Jr. et al. | | 2004/0097797 A1 | 5/2004 | Porges et al. |
| 7,016,715 B2 | 3/2006 | Stetson | | 2004/0098009 A1 | 5/2004 | Boecker et al. |
| 7,020,507 B2 | 3/2006 | Scharf et al. | | 2004/0117891 A1 | 6/2004 | Hannula et al. |
| 7,024,233 B2 | 4/2006 | Ali et al. | | 2004/0147824 A1 | 7/2004 | Diab et al. |
| 7,024,235 B2 | 4/2006 | Melker et al. | | 2004/0158134 A1 | 8/2004 | Diab et al. |
| 7,025,728 B2 | 4/2006 | Ito et al. | | 2004/0162472 A1 | 8/2004 | Berson et al. |

| | | | | | |
|---|---|---|---|---|---|
| 2004/0167381 A1 | 8/2004 | Lichter | DE | 20318882 | 4/2004 |
| 2004/0186358 A1 | 9/2004 | Chernow et al. | EP | 0127947 | 5/1984 |
| 2004/0204637 A1 | 10/2004 | Diab et al. | EP | 00194105 | 9/1986 |
| 2004/0204638 A1 | 10/2004 | Diab et al. | EP | 00204459 | 12/1986 |
| 2004/0204639 A1 | 10/2004 | Casciani et al. | EP | 0 262 779 | 4/1988 |
| 2004/0204865 A1 | 10/2004 | Lee et al. | EP | 0315040 | 10/1988 |
| 2004/0210146 A1 | 10/2004 | Diab et al. | EP | 0314331 | 5/1989 |
| 2004/0215085 A1 | 10/2004 | Schnall | EP | 00352923 | 1/1990 |
| 2004/0236196 A1 | 11/2004 | Diab et al. | EP | 0 360 977 | 4/1990 |
| 2004/0242976 A1 | 12/2004 | Abreu | EP | 00430340 | 6/1991 |
| 2005/0004479 A1 | 1/2005 | Townsend et al. | EP | 0435 500 | 7/1991 |
| 2005/0014999 A1 | 1/2005 | Rahe-Meyer | EP | 0572684 | 5/1992 |
| 2005/0020887 A1 | 1/2005 | Goldberg | EP | 00497021 | 8/1992 |
| 2005/0033131 A1 | 2/2005 | Chen | EP | 0529412 | 8/1992 |
| 2005/0043599 A1 | 2/2005 | O'Mara | EP | 0531631 | 9/1992 |
| 2005/0043600 A1 | 2/2005 | Diab et al. | EP | 0566354 | 4/1993 |
| 2005/0049468 A1 | 3/2005 | Carlson | EP | 0587009 | 8/1993 |
| 2005/0070773 A1 | 3/2005 | Chin | EP | 00630203 | 9/1993 |
| 2005/0075546 A1 | 4/2005 | Samsoondar | EP | 0 572 684 | 12/1993 |
| 2005/0075550 A1 | 4/2005 | Lindekugel | EP | 00615723 | 9/1994 |
| 2005/0085704 A1 | 4/2005 | Schulz | EP | 00702931 | 3/1996 |
| 2005/0090720 A1 | 4/2005 | Wu | EP | 00724860 | 8/1996 |
| 2005/0197548 A1 | 9/2005 | Dietiker | EP | 00793942 | 9/1997 |
| 2005/0197551 A1 | 9/2005 | Al-Ali et al. | EP | 0 864 293 | 9/1998 |
| 2005/0228248 A1 | 10/2005 | Dietiker | EP | 01006863 | 10/1998 |
| 2005/0256386 A1 | 11/2005 | Chan | EP | 01006864 | 10/1998 |
| 2005/0272986 A1 | 12/2005 | Smith | EP | 0875199 | 11/1998 |
| 2005/0277819 A1 | 12/2005 | Kiani et al. | EP | 00998214 | 12/1998 |
| 2006/0009700 A1 | 1/2006 | Brumfeld et al. | EP | 0 898 933 | 3/1999 |
| 2006/0020179 A1 | 1/2006 | Anderson | EP | 0898933 | 3/1999 |
| 2006/0025931 A1 | 2/2006 | Rosen et al. | EP | 0996358 | 1/2002 |
| 2006/0030764 A1 | 2/2006 | Porges | EP | 01332713 | 8/2003 |
| 2006/0058594 A1 | 3/2006 | Ishizuka et al. | EP | 01469773 | 8/2003 |
| 2006/0074280 A1 | 4/2006 | Martis | EP | 1502529 | 7/2004 |
| 2006/0084852 A1 | 4/2006 | Mason et al. | EP | 01491135 | 12/2004 |
| 2006/0084878 A1 | 4/2006 | Banet | FR | 2685865 | 1/1992 |
| 2006/0089547 A1 | 4/2006 | Sarussi | GB | 2 259 545 | 3/1993 |
| 2006/0106294 A1 | 5/2006 | Maser et al. | JP | 63275325 | 11/1988 |
| 2006/0122517 A1 | 6/2006 | Banet | JP | 2013450 | 1/1990 |
| 2006/0129039 A1 | 6/2006 | Lindner | JP | 2111343 | 4/1990 |
| 2006/0155198 A1 | 7/2006 | Schmid | JP | 02 191434 | 7/1990 |
| 2006/0173257 A1 | 8/2006 | Nagai | JP | 2237544 | 9/1990 |
| 2006/0258923 A1 | 11/2006 | Al-Ali et al. | JP | 03 173536 | 7/1991 |
| 2006/0258924 A1 | 11/2006 | Al-Ali et al. | JP | 3170866 | 7/1991 |
| 2006/0258925 A1 | 11/2006 | Al-Ali et al. | JP | 3245042 | 10/1991 |
| 2006/0270920 A1 | 11/2006 | Al-Ali et al. | JP | 4174648 | 6/1992 |
| 2006/0272418 A1 | 12/2006 | Maris et al. | JP | 4191642 | 7/1992 |
| 2006/0272419 A1 | 12/2006 | Maris et al. | JP | 4332536 | 11/1992 |
| 2006/0281983 A1 | 12/2006 | Al-Ali et al. | JP | 3124073 | 3/1993 |
| 2007/0027375 A1 | 2/2007 | Melker et al. | JP | 5049624 | 3/1993 |
| 2007/0032710 A1 | 2/2007 | Raridan et al. | JP | 5049625 | 3/1993 |
| 2007/0032712 A1 | 2/2007 | Raridan et al. | JP | 3115374 | 4/1993 |
| 2007/0032715 A1 | 2/2007 | Eghbal et al. | JP | 05 200031 | 8/1993 |
| 2007/0073117 A1 | 3/2007 | Raridan | JP | 2005/200031 | 8/1993 |
| 2007/0073121 A1 | 3/2007 | Hoarau et al. | JP | 5212016 | 8/1993 |
| 2007/0073122 A1 | 3/2007 | Hoarau | JP | 06 014906 | 1/1994 |
| 2007/0073123 A1 | 3/2007 | Raridan | JP | 06014906 | 1/1994 |
| 2007/0073125 A1 | 3/2007 | Hoarau et al. | JP | 6016774 | 3/1994 |
| 2007/0073126 A1 | 3/2007 | Raridan | JP | 3116255 | 4/1994 |
| 2007/0073128 A1 | 3/2007 | Hoarau | JP | 6029504 | 4/1994 |
| 2007/0078315 A1 | 4/2007 | Kling et al. | JP | 6098881 | 4/1994 |
| 2007/0078316 A1 | 4/2007 | Hoarau | JP | 06 154177 | 6/1994 |
| 2007/0260129 A1 | 11/2007 | Chin | JP | 6269430 | 9/1994 |
| 2007/0260130 A1 | 11/2007 | Chin | JP | 6285048 | 10/1994 |
| 2007/0260131 A1 | 11/2007 | Chin | JP | 7001273 | 1/1995 |
| 2007/0299328 A1 | 12/2007 | Chin et al. | JP | 7124138 | 5/1995 |
| | | | JP | 7136150 | 5/1995 |
| | FOREIGN PATENT DOCUMENTS | | JP | 3116259 | 6/1995 |
| | | | JP | 3116260 | 6/1995 |
| DE | 3516338 | 11/1986 | JP | 7155311 | 6/1995 |
| DE | 37 03 458 | 8/1988 | JP | 7155313 | 6/1995 |
| DE | 3938759 | 5/1991 | JP | 3238813 | 7/1995 |
| DE | 4210102 | 9/1993 | JP | 7171139 | 7/1995 |
| DE | 4423597 | 8/1995 | JP | 3134144 | 9/1995 |
| DE | 19632361 | 2/1997 | JP | 7236625 | 9/1995 |
| DE | 69123448 | 5/1997 | JP | 7246191 | 9/1995 |
| DE | 19703220 | 7/1997 | JP | 8256996 | 10/1996 |
| DE | 19640807 | 9/1997 | JP | 9192120 | 7/1997 |
| DE | 19647877 | 4/1998 | JP | 10216113 | 8/1998 |
| DE | 10030862 | 1/2002 | | | |

| | | |
|---|---|---|
| JP | 10216114 | 8/1998 |
| JP | 10216115 | 8/1998 |
| JP | 10337282 | 12/1998 |
| JP | 11019074 | 1/1999 |
| JP | 11155841 | 6/1999 |
| JP | 11 188019 | 7/1999 |
| JP | 11244268 | 9/1999 |
| JP | 20107157 | 4/2000 |
| JP | 20237170 | 9/2000 |
| JP | 21245871 | 9/2001 |
| JP | 22224088 | 8/2002 |
| JP | 22282242 | 10/2002 |
| JP | 23153881 | 5/2003 |
| JP | 23153882 | 5/2003 |
| JP | 23169791 | 6/2003 |
| JP | 23194714 | 7/2003 |
| JP | 23210438 | 7/2003 |
| JP | 23275192 | 9/2003 |
| JP | 23339678 | 12/2003 |
| JP | 24008572 | 1/2004 |
| JP | 24089546 | 3/2004 |
| JP | 24113353 | 4/2004 |
| JP | 24135854 | 5/2004 |
| JP | 24148069 | 5/2004 |
| JP | 24148070 | 5/2004 |
| JP | 24159810 | 6/2004 |
| JP | 24166775 | 6/2004 |
| JP | 24194908 | 7/2004 |
| JP | 24202190 | 7/2004 |
| JP | 24248819 | 9/2004 |
| JP | 24248820 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 24337605 | 12/2004 |
| JP | 24344367 | 12/2004 |
| JP | 24351107 | 12/2004 |
| JP | 25034472 | 2/2005 |
| WO | WO8909566 | 10/1989 |
| WO | WO 90/01293 | 2/1990 |
| WO | WO 90/04352 | 5/1990 |
| WO | WO 91/01678 | 2/1991 |
| WO | WO 91/11137 | 8/1991 |
| WO | WO 92/00513 | 1/1992 |
| WO | WO 92/21281 | 12/1992 |
| WO | WO 93/09711 | 5/1993 |
| WO | WO 93/13706 | 7/1993 |
| WO | WO 93/16629 | 9/1993 |
| WO | WO 94/03102 | 2/1994 |
| WO | WO 94/23643 | 10/1994 |
| WO | WO 95/02358 | 1/1995 |
| WO | WO 95/12349 | 5/1995 |
| WO | WO 95/16970 | 6/1995 |
| WO | WO 96/13208 | 5/1996 |
| WO | WO 96/39927 | 12/1996 |
| WO | WO 97/36536 | 10/1997 |
| WO | WO 97/36538 | 10/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 0116577 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 04/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |
| WO | WO 2006/132862 | 12/2006 |

OTHER PUBLICATIONS

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Aoyagi, T., et al.; "Analysis of Motion Artifacts in Pulse Oximetry," *Japanese Society ME*, vol. 42, p. 20 (1993) (Article in Japanese—contains English summary of article).

Aoyagi, T., et al.; "Pulse Oximeters: background, present and future," *Neonatal Care*, vol. 13, No. 7, pp. 21-27 (2000) (Article in Japanese—contains English summary of article).

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Barreto, Armando B., et al.; "Adaptive LMS Delay Measurement in dual Blood Volume Pulse Signals for Non-Invasive Monitoring," *IEEE*, pp. 117-120 (1997).

Belal, Suliman Yousef, et al.; "A fuzzy system for detecting distorted plethysmogram pulses in neonates and paediatric patients," *Physiol. Meas.*, vol. 22, pp. 397-412 (2001).

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Branche, Paul C., et al.; "Measurement Reproducibility and Sensor Placement Considerations in Designing a Wearable Pulse Oximeter for Military Applications," 2 pgs. (2004).

Buschman, J.P., et al.; "Principles and Problems of Calibration of Fetal Oximeters," *Biomedizinische Technik*, vol. 42, pp. 265-266 (1997).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Crespi, F., et al.; "Near infrared oximeter prototype for non-invasive analysis of rat brain oxygenation," *Optical Sensing, Proceedings of SPIE*, vol. 5459, pp. 38-45 (2004).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Cyrill, D., et al.; "Adaptive Comb Filter for Quasi-Periodic Physiologic Signals," Proceedings of the $25^{th}$ Annual International Conference of the IEEE EMBS, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

DeKock, Marc; "Pulse Oximetry Probe Adhesive Disks: a Potential for Infant Aspiration," *Anesthesiology*, vol. 89, pp. 1603-1604 (1998).

Earthrowl-Gould, T., et al.; "Chest and abdominal surface motion measurement for continuous monitoring of respiratory function," *Proc. Instn Mech Engrs*, V215, Part H; pp. 515-520 (2001).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the $20^{th}$ Annual International conference of the IEEE Engineering in Medicine and Biology Society*, vol. 20, No. 6, pp. 3072-3075 (1998).

Edrich, Thomas, et al.; "Pulse Oximetry: An Improved in Vitro Model that Reduces Blood Flow-Related Artifacts," *IEEE Transactions on Biomedical Engineering*, vol. 47, No. 3, pp. 338-343 (Mar. 2000).

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Ferrell, T.L., et al.; "Medical Telesensors," *SPIE*, vol. 3253, pp. 193-198 (1998).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Goldman, Julian M.; "Masimo Signal Extraction Pulse Oximetry," *Journal of Clinical Monitoring and Computing*, vol. 16, pp. 475-483 (2000).

Gosney, S., et al.; "An alternative position for the pulse oximeter probe," *Anaesthesia*, vol. 56, p. 493 (2001).

Gostt, R., et al.; "Pulse Oximetry Artifact Recognition Algorithm for Computerized Anaesthetic Records," *Journal of Clinical Monitoring and Computing Abstracts*, p. 471 (2002).

Hamilton, Patrick S., et al.; "Effect of Adaptive Motion-Artifact Reduction on QRS Detection," *Biomedical Instrumentation & Technology*, pp. 197-202 (undated).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Hayes, Matthew J., et al.; "Artifact reduction in photoplethysmography," *Applied Optics*, vol. 37, No. 31, pp. 7437-7446 (Nov. 1998).

Hayes, Matthew J., et al.; "Quantitative evaluation of photoplethysmographic artifact reduction for pulse oximetry," *SPIE*, vol. 3570, pp. 138-147 (Sep. 1998).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Ikeda, Kenji, et al.; "Improvement of Photo-Electric Plethysmograph Applying Newly Developed OptoElectronic Devices," *IEEE Tencon*, pp. 1109-1112 (1999).

Irie, A., et al.; "Respiration Monitors — Pulse Oximeters," *Neonatal Care*, vol. 15, No. 12, pp. 78-83 (2002) (Article in Japanese—contains English summary of article).

Itoh, K., et al.; "Pulse Oximeter," *Toyaku Zasshi* (Toyaku Journal), vol. 25, No. 8, pp. 50-54 (2003) (Article in Japanese—contains English summary of article).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Hayoz, J., et al.; "World's First Combined digital Pulse Oximetry Pulse Oximetry and Carbon Dioxide Tension Ear Sensor", *Abstracts*, A6, p. S103. (undated).

Huang, J., et al.; "Low Power Motion Tolerant Pulse Oximetry," *Abstracts*, A7, p. S103. (undated).

Johansson, A.; "Neural network for photoplethysmographic respiratory rate monitoring," *Medical & Biological Engineering & Computing*, vol. 41, pp. 242-248 (2003).

Johnston, W.S., et al.; "Extracting Breathing Rate Infromation from a Wearable Reflectance Pulse Oximeter Sensor," *Proceedings of the $26^{th}$ Annual International conference of the IEEE EMBS*, San Francisco, California; Sep. 1-5, 2004; pp. 5388-5391.

Johnston, William S., et al.; "Effects of Motion Artifacts on helmet-Mounted Pulse Oximeter Sensors," 2 pgs. (2004).

Jopling, Michae W., et al.; "Issues in the Laboratory Evaluation of Pulse Oximeter Performance," *Anesth Analg*, vol. 94, pp. S62-S68 (2002).

Jovanov, E., et al.; "Reconfigurable intelligent Sensors for Health Monitoring: A case Study of Pulse Oximeter Sensor," *Proceedings o the $26^{th}$ Annual International conference of the IEEE EMBS*, San Francisco, California, Sep. 1-5, 2004, pp. 4759-4762.

Kaestle, S.; "An Algorithm for Reliable Processing of Pulse Oximetry Signals Under strong Noise Conditions," *Dissertation Book*, Lubeck University, Germany (1999).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform," pp. II-310-II-311 (undated).

Kocher, Serge, et al.; "Performance of a Digital $PCO_2/SPO_2$ Ear Sensor," *Journal of Clinical Monitoring and Computing*, vol. 18, pp. 75-59 (2004).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

König, Volker, et al.; "Reflectance Pulse Oximetry—Principles and Obstetric Application in the Zurich System," *Journal of Clinical Monitoring and Computing*, vol. 14, pp. 403-412 (1998).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Leahy, Martin J., et al.; "Sensor Validation in Biomedical Applications," *IFAC Modelling and Control in Biomedical Systems*, Warwick, UK; pp. 221-226 (1997).

Lebak, J.W., et al.; "Implementation of a Standards-Based Pulse Oximeter on a Wearable, Embedded Platform," *Proceeding of the $25^{th}$ Annual International Conference of the IEEE EMBS*, Cancun, Mexico, Sep. 17-21, 2003; pp. 3196-3198.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lee, C.M., et al.; "Reduction of Motion Artifacts from Photoplethysmographic Records Using a Wavelet Denoising Approach," *IEEE*, pp. 194-195 (undated).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Lutter, N., et al.; "Comparison of Different Evaluation Methods for a Multi-wavelength Pulse Oximeter," *Biomedizinische Technik*, vol. 43, (1998).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

Masin, Donald I., et al.; "Fetal Transmission Pulse Oximetry," *Proceedings 19$^{th}$ International Conference IEEE/EMBS*, Oct. 30-Nov. 2, 1997; pp. 2326-2329.

Matsuzawa, Y., et al.; "Pulse Oximeter," *Home Care Medicine*, pp. 42-45 (Jul. 2004); (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Matthews, Nora S. et al.; "An evaluation of pulse oximeters in dogs, cats and horses," *Veterinary Anaesthesia and Analgesia*, vol. 30, pp. 3-14 (2003).

Mendelson, Y., et al.; "Measurement Site and Photodetector Size Considerations in Optimizing Power Consumption of a Wearable Reflectance Pulse Oximeter," *Proceedings of the 25$^{th}$ Annual International conference of the IEEE EMBS*, Cancun, Mexico, Sep. 17-21, 2003; pp. 3016-3019.

Nagl, L., et al.; "Wearable Sensor System for Wireless State-of-Health Determination in Cattle," *Proceeding of the 25$^{th}$ Annual International Conference of the IEEE EMBS*, Cancun, Mexico, Sep. 17-21, 2003; pp. 3012-3015.

Nakagawa, M., et al.; "Oxygen Saturation Monitor," *Neonatal Monitoring*, vol. 26, No. 5, pp. 536-539 (2003) (Article in Japanese—contains English summary of article).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Nogawa, Masamichi, et al.; "A Novel Hybrid Reflectance Pulse Oximater Sensor with improved Linearity and General Applicability to Various Portions of the Body," *Proceedings of the 20$^{th}$ Annual International Conference of the IEEE Engineering in Medicine and Biology Society*, vol. 20, No. 4, pp. 1858-1861 (1998).

Nuhr, M., et al.: "Forehead SpO$_2$ monitoring compared to finger SpO$_2$ recording in emergency transport," *Anaesthesia*, vol. 59, pp. 390-393 (2004).

Odagiri, Y.; "Pulse Wave Measuring Device," *Micromechatronics*, vol. 42, No. 3, pp. 6-11 (undated) (Article in Japanese—contains English summary of article).

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

P. Lang, et al.; "Signal Identification and Quality Indicator™ for Motion Resistant Pulse Oximetry," *Abstracts*, A10, p. S105. (undated).

Pickett, John, et al.; "Pulse Oximetry and PPG Measurements in Plastic Surgery," *Proceedings—19$^{th}$ International Conference—IEEE/EMBS*, Chicago, Illinois, Oct. 30-Nov. 2, 1997, pp. 2330-2332.

Plummer, John L., et al.; "Identification of Movement Artifact by the Nellcor N-200 and N-3000 Pulse Oximeters," *Journal of clinical Monitoring*, vol. 13, pp. 109-113 (1997).

Poets, C. F., et al.; "Detection of movement artifact in recorded pulse oximeter saturation," *Eur. J. Pediatr.*; vol. 156, pp. 808-811 (1997).

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Pujary, C., et al.; "Photodetector Size Considerations in the Design of a Noninvasive Reflectance Pulse Oximeter for Telemedicine Applications," *IEEE*, pp. 148-149 (2003).

Relente, a.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Reuss, James L.; "Factors Influencing Fetal Pulse Oximetry Performance," *Journal of clinical Monitoring and Computing*, vol. 18, pp. 13-14 (2004).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796-2799.

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rhee, Sokwoo, et al.; "The Ring Sensor: a New Ambulatory Wearable Sensor for Twenty-Four Hour Patient Monitoring," *Proceedings of the 20$^{th}$ annual International Conference of the IEEE Engineering in Medicine and Biology Society*, vol. 20, No. 4, pp. 1906-1909 (Oct. 1998).

Rheineck-Leyssius, Aart T., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Schulz, Christian Eric; "Design of a Pulse Oximetry Sensor Housing Assembly," California State University Master's Thesis, *UMI Dissertation Services*, UMI No. 1401306, (May 2000) 63 pages.

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

"Smaller Product, Tighter Tolerances Pose Dispensing Challenges for Medical Device Manufacturer," *Adhesives Age*, pp. 40-41 (Oct. 1997).

Soto, Denise A.; "A Comparative Study of Pulse Oximeter Measurements: Digit Versus Earlobe," Master of Science Thesis, California State University Dominguez Hills, May 1997, 46 pgs.

Spigulis, Janis, et al.; "Optical multi-channel sensing of skin blood pulsations," *Optical Sensing, Proceedings of SPIE*, vol. 5459, pp. 46-53 (2004).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Todd, Bryan, et al.; "The Identification of Peaks in Physiological Signals," Computers and *Biomedical Research*, vol. 32, pp. 322-335 (1999).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Urquhart, C., et al.; "Ear probe pulse oximeters and neonates," *Anaesthesia*, vol. 60, p. 294 (2005).

Vicenzi, Martin N.; "Transesophageal versus surface pulse oximetry in intensive care unit patients," *Crit. Care Med.*; vol. 28, No. 7, pp. 2268-2270 (2000).

Vincente, L.M., et al.; "Adaptive Pre-Processing of Photoplethysmographic Blood Volume Pulse Measurements," pp. 114-117 (1996).

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Wendelken, Suzanne, et al.; "The Feasibility of Using a Forehead Reflectance Pulse Oximeter for Automated Remote Triage," *IEEE*, pp. 180-181 (2004).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Yang, Boo-Ho, et al.; "Development of the ring sensor for healthcare automation," *Robotics and Autonomous Systems*, vol. 30, pp. 273-281 (2000).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanes3—contains English summary of article).

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

\* cited by examiner

MEDICAL SENSOR FOR REDUCING MOTION ARTIFACTS AND TECHNIQUE FOR USING THE SAME

CROSS-REFERENCES TO THE RELATED APPLICATIONS

This application is a continuation of U.S. patent application Ser. No. 11/225,295, filed Sep. 12, 2005, the disclosure of which is hereby incorporated by reference in its entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings depend on pulsation of blood through the tissue. Thus, any event that interferes with the ability of the sensor to detect that pulsation can cause variability in these measurements. Motion artifacts occur when a patient's movements cause interference in the signal detected by the sensor. Motion artifacts can also occur in response to outside forces acting on the sensor. For example, a patient may be jostled by healthcare workers in emergency room settings. The type of force acting on a sensor will determine the nature of the motion artifact.

Generally, sensors are vulnerable to motion artifacts when the optical distance, or path length, between a sensor's emitter and detector varies due to an undesired mechanical change in the conformation of the sensor while in use. The mechanical deformation of the sensor may be in the form of a compression of the sensor, causing a decrease in path length. Alternately, a sensor may flex or move in a manner that increases the distance between an emitter and detector, resulting in an increase in path length. In any case, variability in the optical path length due to motion can cause motion artifacts and obscure the desired pulse oximetry signal.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes a sensor body, and an emitter and a detector disposed on the sensor body. The sensor also includes a motion damping structure associated with the sensor body, whereby the motion damping structure is adapted to damp a force experienced by the sensor body.

There is also provided a pulse oximetry system that includes: a pulse oximetry monitor; and a pulse oximetry sensor adapted to be operatively coupled to the monitor. The sensor includes a sensor body, and an emitter and a detector disposed on the sensor body. The sensor also includes a motion damping structure associated with the sensor body, whereby the motion damping structure is adapted to damp a force experienced by the sensor body.

There is also provided a method of operating a sensor that includes damping a mechanical force affecting a sensor such that an effective force experienced by at least one of a emitter or a detector is less than the mechanical force.

There is also provided a method of manufacturing a sensor that includes providing a sensor body on which an emitter and a detector are disposed. The method also includes providing a motion damping structure disposed on the sensor body.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that reduce motion artifacts by damping the effects of patient movement or outside forces. For example, sensors are provided that have various motion damping mechanisms adapted to reduce the effect of motion or outside forces on a pulse oximetry measurement.

Motion artifacts in pulse oximetry are often generated by the movement of the pulse oximetry sensor relative to the optically probed tissue, which is typically caused by patient movement. Because pulse oximetry is often used in settings where it is difficult to prevent patient motion, it is desirable to provide a mechanism for reducing the effects of motion on the pulse oximetry measurement. For example, a squeezing motion by a patient may mechanically deform a sensor, causing the sensor's emitter and detector to change position relative to one another, resulting in a motion artifact. The squeezing motion may be damped by converting the mechanical energy of patient movement into thermal energy by damping the force with an impact-absorbing fluid or solid, thus dissipating the force and reducing mechanical deformation of the sensor. The force of squeezing may be damped such that the effective force experienced by the sensor's emitter and/or detector is reduced, and the relative change in the position of the emitter relative to the detector is also reduced. Similarly, outsides forces, such as the mechanical force of an object pressing against a sensor, can be damped by absorbing the force such that the effective force experienced by the sensor components is reduced.

Mechanical forces, including those caused by translational and/or kinetic energy of an object, may be impeded by opposing forces. Specifically, as a force acts on a pulse oximetry sensor, it is opposed by the inertia of the sensor as well as the opposing force of a damper. The amplitude of the mechanical energy of movement is attenuated through energy lost to inertia and damping. For example, energy may be lost to viscous damping with a fluid, or by yielding or plastic straining of a damping material. Additionally, some energy will be converted to thermal energy through frictional forces.

Figure 1A:
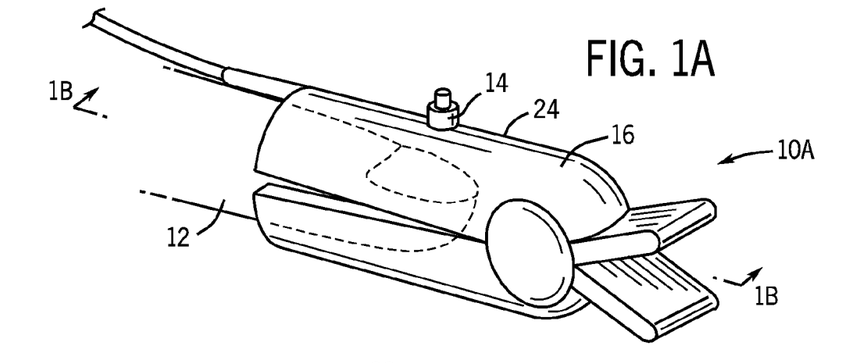
FIG. 1A illustrates a perspective view of an exemplary embodiment of a clip-style pulse oximetry sensor featuring a dashpot.
Figure 1B:
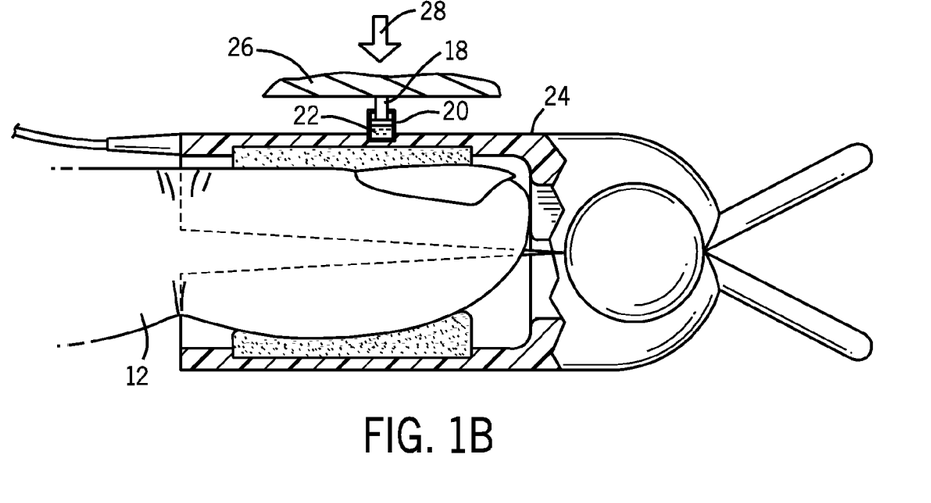
FIG. 1B illustrates a cross-sectional view of the pulse oximetry sensor of FIG. 1A applied to a patient digit that is pressing against an object.

Sensors are disclosed herein having a motion damping mechanism to reduce the effect of motion or outside forces on the measurements of physiological parameters, such as pulse oximetry measurements. FIG. 1A illustrates an exemplary clip-type sensor 10A appropriate for use on a patient's digit 12. The sensor 10A has a dashpot 14 disposed on the sensor body 16, a cross-sectional view of which is illustrated in FIG. 1B. A dashpot 14 is a mechanical device used to damp motion that includes a piston 18 that moves through a cylinder 20 containing a fluid 22. The dashpot 14 is partially embedded in the sensor body 16 such that the piston 18 protrudes from the sensor body 16 on a surface 24 that does not contact the sensor site of the patient's tissue during normal use. A force applied to the piston 18, such as tapping against an object 26, causes the piston 18 to move through the fluid 22 in the direction shown by arrow 28. As the piston 18 pushes through the fluid 22, the mechanical energy of the force acting on the piston 18 is converted into thermal energy. The damping force is proportional to the velocity of the piston 18 and the viscosity of the fluid 22 through which the piston moves. Thus, the dashpot 14 damps motion caused by tapping or pressing the sensor 10A against an object 26.

In other embodiments (not shown), the sensor 10A may have multiple dashpots 14 disposed on the sensor body 16 on the surface 24 that does not contact the sensor site of the patient's tissue during normal use. It may be advantageous to provide motion damping mechanisms on multiple sides of the sensor 10A, as it is difficult to predict the types of motion that the sensor 10A may experience. For example, dashpots 14 may be distributed on the sensor body 16 in locations directly opposing each other across the digit 12. Further, it should be understood that a dashpot 14 according to the present technique may be adapted to damp forces applied at various angles. The piston 18 may be adapted move through the fluid 22 at an angle that corresponds to the angle with which the force was applied.

Figure 2:
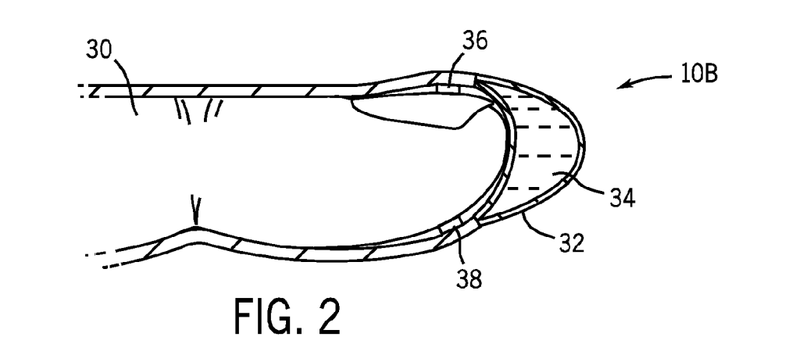
FIG. 2 illustrates a cross-sectional view of an exemplary embodiment of a bandage-style pulse oximetry sensor applied to a patient's digit, whereby the sensor includes an impact-absorbing chamber at one end of the sensor.

In certain embodiments, a fluid may used to damp mechanical energy by other techniques. For reasons related to total sensor weight, it may be desirable to employ a lightweight motion damping device in conjunction with disposable sensors. For example, FIG. 2 illustrates a bandage-type sensor 10B applied to a patient digit 30. The sensor 10B has an impact-absorbing chamber 32 that contains a fluid 34. As depicted, the impact-absorbing chamber 32 is disposed on the sensor 10B such that it correlates with the fingertip region of the digit 30. The fluid 34 in the impact-absorbing chamber 32 damps energy caused by pressing or tapping a fingertip against an object. The impact-absorbing chamber 32 is flexible and not completely filled with fluid, and is thus compressible in response to an applied force. The mechanical energy of the pressing or tapping is damped through conversion to thermal energy and/or absorbed by the physical deformation of the fluid in an amount proportional to the force applied. Thus, the motion is damped and the effective force experienced by the emitter 36 and the detector 38 is reduced as a consequence.

Figure 3:
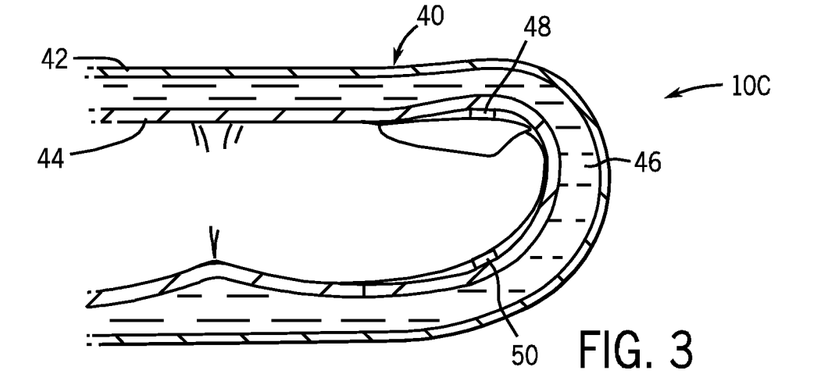
FIG. 3 illustrates a perspective view of an alternate exemplary embodiment of a bandage-style pulse oximetry sensor with a fluid-filled impact-absorbing chamber disposed along the body of the sensor.

In another embodiment, as shown in FIG. 3, an impact-absorbing chamber 42 may be disposed on a sensor 10C such that the impact-absorbing chamber 42 covers the surface 40 of the sensor body 44 that does not contact the tissue during normal use. The fluid 46 in the impact-absorbing chamber 42 will physically impede a finger squeezing motion as well as damp the mechanical energy associated with the motion. As the energy of squeezing is absorbed by the fluid 46, the sensor 10C remains substantially stable. As a consequence, the emitter 48 and the detector 50 also remain substantially unaffected by the motion.

Figure 4:
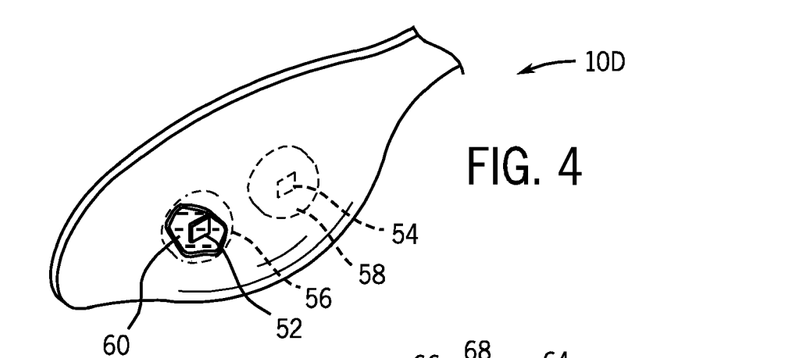
FIG. 4 illustrates a perspective view of an exemplary embodiment of a forehead pulse oximetry sensor whereby the emitter and detector are disposed within impact-absorbing chambers.

It is also contemplated that a fluid may damp mechanical energy to reduce its direct action on an emitter 52 or a detector 54. FIG. 4 illustrates a reflectance-type sensor 10D adapted for use on a patient's forehead. The sensor 10D has impact-absorbing chambers 56 and 58 containing a fluid 60. The impact-absorbing chambers 56 and 58 enclose an emitter 52 and a detector 54, respectively. The emitter 52 and the detector 54 are surrounded by the fluid 60, which absorbs outside forces, thereby reducing the transmission of outside forces to the emitter 52 and the detector 54. The impact-absorbing chambers 56 and 58 also protect the emitter 52 and the detector 54 from damage during the period of use of the sensor 10D. Such an arrangement may be advantageous in outpatient situations in which it is contemplated that a patient may be ambulatory, and the sensor 10C may be subject to higher-than-normal outside forces.

Figure 5A:
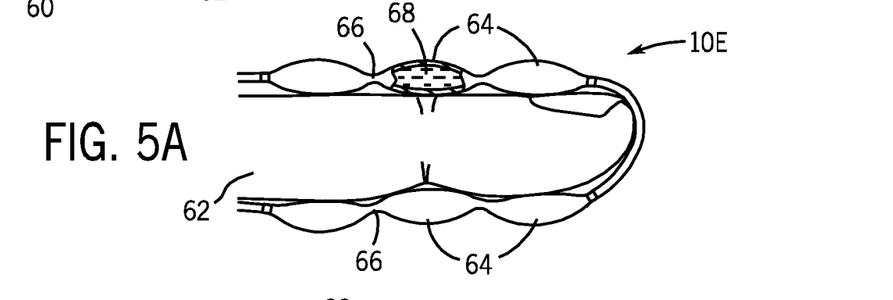
FIG. 5A illustrates a cross-sectional view of an exemplary embodiment of a bandage-style pulse oximetry sensor having a series of interconnected impact-absorbing chambers.
Figure 5B:
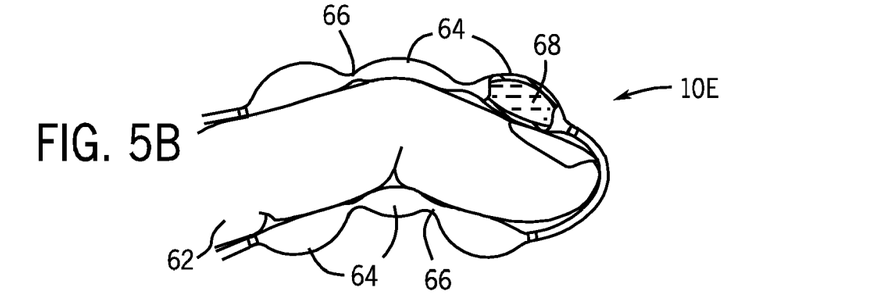
FIG. 5B illustrates a cross-sectional view of the pulse oximetry sensor of FIG. 5A applied to a patient digit that is flexed at the first finger joint.

In another embodiment, FIG. 5A illustrates an exemplary bandage-style sensor 10E adapted for use on a digit 62. The sensor 10E has a plurality of impact-absorbing chambers 64 connected by respective orifices 66, wherein the orifices 66 are sized so as to restrict the flow rate of a fluid 68 between the impact-absorbing chambers 64. As shown in FIG. 5B, as the digit 62 moves in a squeezing motion, the fluid 68 passes through the orifices 66 and is redistributed through the impact-absorbing chambers 64 in response to the movement. The impact-absorbing chambers 64 are partially full of the fluid 68. The redistribution of the fluid 68 serves to damp the energy generated by the digit 62 moving in space. Specifically, the force of the digit 62 movement is opposed by the force required to push the fluid 68 through the orifices 66. The damped force experienced by the sensor 10E is thus reduced by roughly the amount of the opposing force provided by the damping mechanism.

The fluid (e.g. fluid 22, fluid 34, fluid 46, fluid 60, or fluid 68) described in the above embodiments may be any suitable fluid with the appropriate rheological properties for damping mechanical energy, such as a viscoelastic fluid or gel. In certain embodiments, the fluid may be air or other gases and gas mixtures. In other embodiments, the fluid may be an oil or liquid, such as mineral oil. Other examples of suitable fluids include, but are not limited to, polyethylene glycol, liquid silicone, magnetorheological fluids, and polyurethane polymer gels. It is contemplated that the fluid may be a mixture of liquid and gas. In certain embodiments, it may be desirable employ a gas or gas mixture for reasons related to cost, manufacturing convenience, and total sensor weight. In situations where a sensor may be exposed to more extreme outside forces, it may be desirable to employ a viscoelastic oil, as oils generally provide more efficient damping than gases.

Figure 6A:
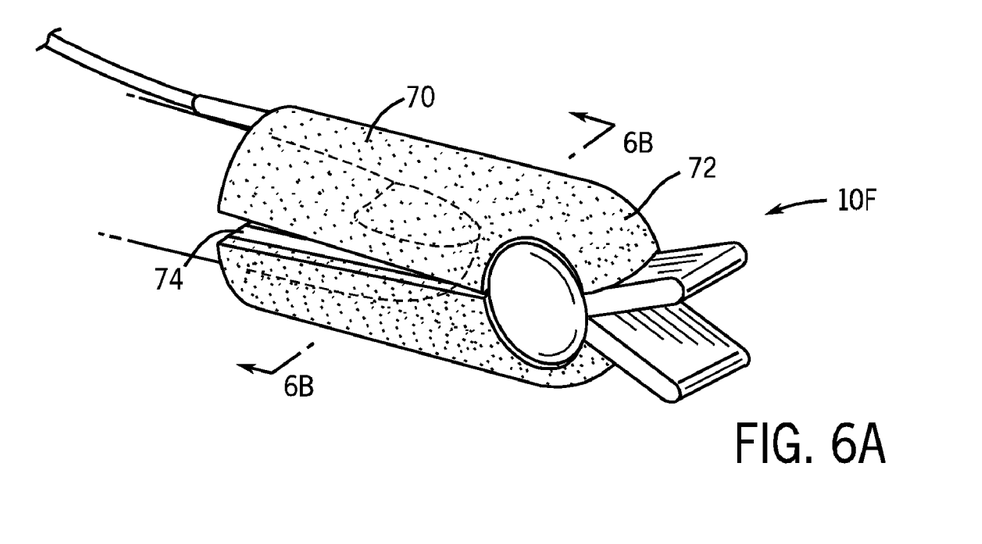
FIG. 6A illustrates a perspective view of an embodiment of an exemplary clip-style pulse oximetry sensor with an impact-absorbing foam disposed on the surface that does not contact a patient's tissue during normal use according to the present invention.
Figure 6B:
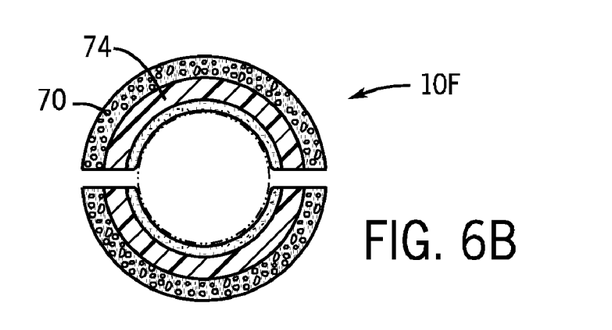
FIG. 6B illustrates a cross-sectional view of the pulse oximetry sensor of FIG. 6A.

In certain embodiments, impact-absorbing solids and/or foams with viscoelastic properties may be appropriate for mechanical damping of motion to reduce motion artifacts in a pulse oximetry sensor. For example, a clip-style sensor 10F is illustrated in FIG. 6A that has an impact-absorbing foam 70 disposed over a non-tissue-contacting surface 72 of the sensor body 74. FIG. 6B is a cross-sectional view of the sensor 10F. The impact-absorbing foam 70 dissipates the effect of an outside force on the sensor 10F. In another embodiment (not shown), the impact absorbing foam 70 is disposed on the tissue-contacting surface of the sensor 10F. Impact-absorbing solids and foams according to the present invention include, but are not limited to, neoprene, silicone, rubber, Sorbothane® (available from Sorbothane, Incorporated), and ISODAMP® SD or CONFOR® foams (available from E-A-R Specialty Composites).

Figure 7:
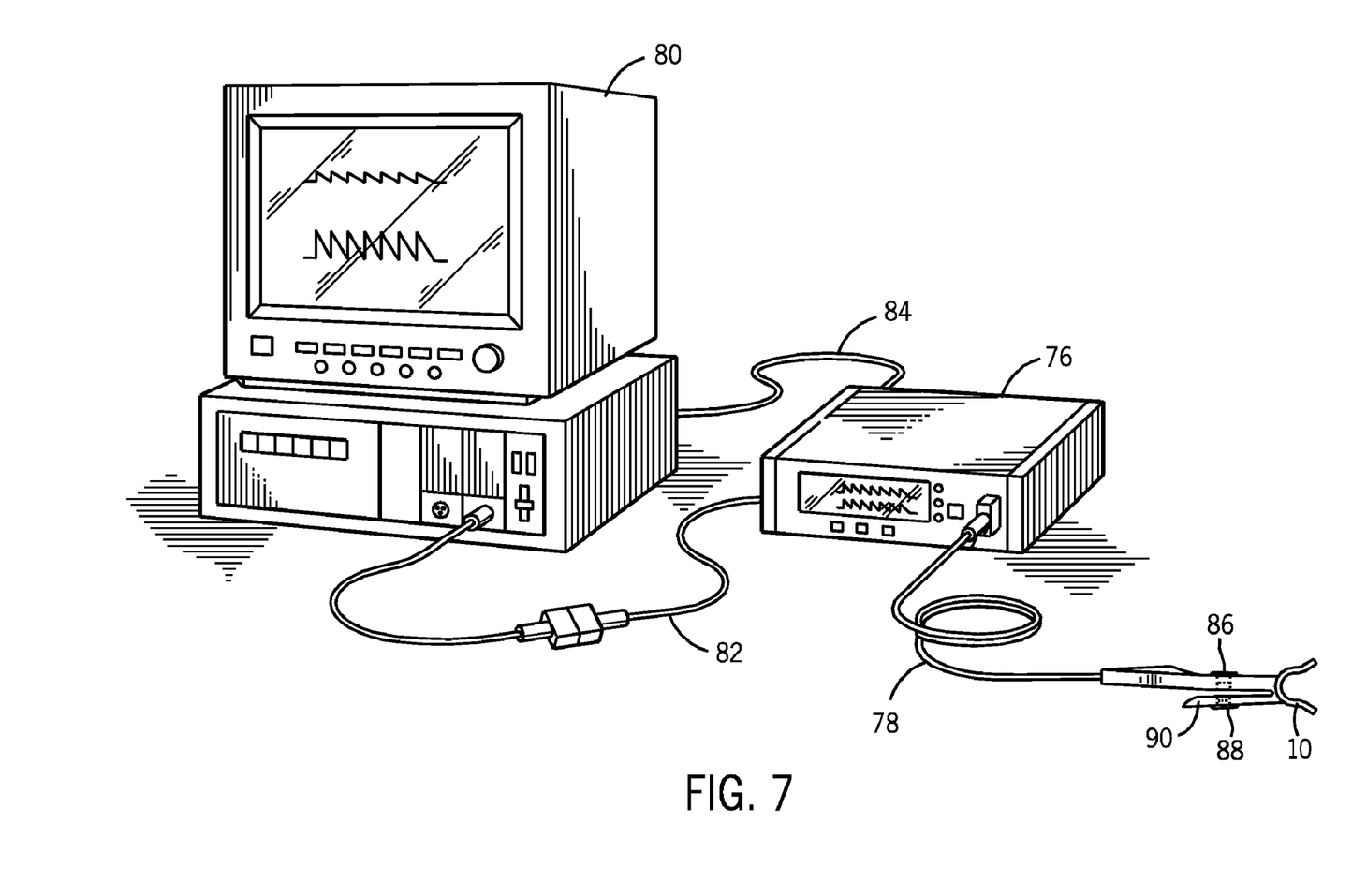
FIG. 7 illustrates a pulse oximetry system coupled to a multi-parameter patient monitor and a sensor according to embodiments of the present invention.

A sensor, illustrated generically as a sensor 10, may be used in conjunction with a pulse oximetry monitor 76, as illustrated in FIG. 7. It should be appreciated that the cable 78 of the sensor 10 may be coupled to the monitor 76 or it may be coupled to a transmission device (not shown) to facilitate wireless transmission between the sensor 10 and the monitor 76. The monitor 76 may be any suitable pulse oximeter, such as those available from Nellcor Puritan Bennett Inc. Furthermore, to upgrade conventional pulse oximetry provided by the monitor 76 to provide additional functions, the monitor 76 may be coupled to a multi-parameter patient monitor 80 via a cable 82 connected to a sensor input port or via a cable 84 connected to a digital communication port.

The sensor 10 includes an emitter 86 and a detector 88 that may be of any suitable type. For example, the emitter 86 may be one or more light emitting diodes adapted to transmit one or more wavelengths of light in the red to infrared range, and the detector 88 may be a photodetector selected to receive light in the range or ranges emitted from the emitter 86. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The emitter 86 and the detector 88 may be disposed on a sensor body 90, which may be made of any suitable material, such as plastic, foam, woven material, or paper. Alternatively, the emitter 86 and the detector 88 may be remotely located and optically coupled to the sensor 10 using optical fibers. In the depicted embodiments, the sensor 10 is coupled to a cable 78 that is responsible for transmitting electrical and/or optical signals to and from the emitter 86 and detector 88 of the sensor 10. The cable 78 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 86 and detector 88 that are typically placed on opposing sides of the sensor site. If the sensor site is a fingertip, for example, the sensor 10 is positioned over the patient's fingertip such that the emitter 86 and detector 88 lie on either side of the patient's nail bed. In other words, the sensor 10 is positioned so that the emitter 86 is located on the patient's fingernail and the detector 88 is located 180° opposite the emitter 86 on the patient's finger pad. During operation, the emitter 86 shines one or more wavelengths of light through the patient's fingertip and the light received by the detector 88 is processed to determine various physiological characteristics of the patient. In each of the embodiments discussed herein, it should be understood that the locations of the emitter 86 and the detector 88 may be exchanged. For example, the detector 88 may be located at the top of the finger and the emitter 86 may be located underneath the finger. In either arrangement, the sensor 10 will perform in substantially the same manner.

Reflectance type sensors generally operate under the same general principles as transmittance type sensors. However, reflectance type sensors include an emitter 86 and detector 88 that are typically placed on the same side of the sensor site. For example, a reflectance type sensor may be placed on a patient's fingertip or forehead such that the emitter 86 and detector 88 lie side-by-side. Reflectance type sensors detect light photons that are scattered back to the detector 88.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
a bandage-type sensor body;
an emitter and a detector disposed on the sensor body and adapted to be positioned proximate to a tissue of a patient; and
a motion damping structure disposed on an exterior surface of the sensor body, such that the motion damping structure is visible and faces away from the tissue when the sensor is applied to the patient, wherein the motion damping structure is capable of damping a force experienced by the sensor body, such that the motion damping structure moves at least partially independently of the emitter and the detector when an external force is applied to the motion damping structure and wherein the motion damping structure comprises a chamber, the chamber comprising a fluid layer and a retaining layer, such that the fluid layer is between the retaining layer and the sensor body and comprises a viscoelastic material.

2. The sensor, as set forth in claim 1, wherein the sensor comprises at least one of a pulse oximetry sensor or a sensor for measuring a water fraction.

3. The sensor, as set forth in claim 1, wherein the emitter comprises at least one light emitting diode, and wherein the detector comprises at least one photodetector.

4. The sensor, as set forth in claim 1, wherein the motion damping structure is only disposed about a region correlating to a tip of a digit of the patient.

5. The sensor, as set forth in claim 1, wherein the motion damping structure is disposed between the emitter and the detector.

6. The sensor, as set forth in claim 1, wherein the fluid comprises a gel.

7. A pulse oximetry system comprising:
a pulse oximetry monitor; and
a pulse oximetry sensor adapted to be operatively coupled to the monitor, the sensor comprising:
a bandage-type sensor body;
an emitter and a detector disposed on the sensor body and adapted to be positioned proximate to a tissue of a patient; and
a motion damping structure disposed on an exterior surface of the sensor body, such that the motion damping structure is visible and faces away from the tissue when the sensor is applied to the patient, wherein the motion damping structure is capable of damping a force experienced by the sensor body, and wherein the motion damping structure comprises a chamber, the chamber comprising a fluid layer and a retaining layer, such that the fluid layer is between the retaining layer and the sensor body and comprises a viscoelastic material.

8. The system, as set forth in claim 7, wherein the emitter comprises at least one light emitting diode, and wherein the detector comprises at least one photodetector.

9. The system, as set forth in claim 7, wherein the motion damping structure substantially covers the exterior surface of the sensor body.

10. A sensor comprising:
a conformable sensor body;
an emitter and a detector disposed on an interior surface of the sensor body, wherein the interior surface is adapted to be proximate to a patient's tissue when the sensor is applied; and
a motion damping structure comprising a plurality of chambers disposed on an exterior surface the sensor body, wherein the exterior surface of the sensor body is opposite the interior surface, and wherein the motion damping structure is capable of damping a force experienced by the sensor body and comprises a viscoelastic material, such that the motion damping structure moves at least partially independently of the emitter and the detector when an external force is applied to the motion damping structure, and wherein the plurality of chambers are in fluid communication with one another.

11. The sensor, as set forth in claim 10, wherein the sensor comprises at least one of a pulse oximetry sensor or a sensor for measuring a water fraction.

12. The sensor, as set forth in claim 10, wherein the emitter comprises at least one light emitting diode, and wherein the detector comprises at least one photodetector.

13. The sensor, as set forth in claim 10, wherein the sensor body comprises a plastic.

14. The sensor, as set forth in claim 10, wherein the motion damping structure substantially covers the exterior surface.

15. The sensor, as set forth in claim 10, wherein the motion damping structure is configured to be disposed about a dorsal region of a digit of the patient.

16. The sensor, as set forth in claim 10, wherein the motion damping structure is configured to be disposed about a region corresponding to a joint of a digit of the patient.

17. The sensor, as set forth in claim 10, wherein the motion damping structure is not disposed between the emitter and the detector.

* * * * *